United States Patent [19]

Mathew et al.

[11] Patent Number: 5,405,930

[45] Date of Patent: Apr. 11, 1995

[54] DI-, TRI- AND TETRAFUNCTIONAL METHYL ISOBUTYL AND METHYL AMYL KETOXIME-BASED SILANES

[75] Inventors: Chempolil T. Mathew, Randolph; Edward T. Asirvatham, Chatham; Jeffrey A. Knepper, Somerville; Dale R. Flackett, Somerset, all of N.J.

[73] Assignee: AlliedSignal Inc., Morristown, N.J.

[21] Appl. No.: 158,660

[22] Filed: Nov. 29, 1993

Related U.S. Application Data

[63] Continuation-in-part of Ser. No. 947,015, Sep. 17, 1992, Pat. No. 5,359,108.

[51] Int. Cl.$^6$ .................... C08G 77/04; C07F 7/04
[52] U.S. Cl. ........................................ 528/34; 556/422
[58] Field of Search ........................... 556/422; 528/34

[56] References Cited

U.S. PATENT DOCUMENTS

| | | | |
|---|---|---|---|
| 3,189,576 | 6/1965 | Sweet | 260/46.5 |
| 3,826,782 | 7/1974 | Lengnick | 260/46.5 E |
| 4,033,991 | 7/1977 | Shinohara et al. | 260/448.2 E |
| 4,503,210 | 3/1985 | Von Au et al. | 528/33 |
| 4,766,231 | 8/1988 | Zoche | 556/422 |
| 4,925,964 | 5/1990 | Zoche | 556/422 |
| 5,087,718 | 2/1992 | Zoche | 556/422 |

FOREIGN PATENT DOCUMENTS

0369359A3  5/1990  European Pat. Off. .

OTHER PUBLICATIONS

Goel, et al., Untersuchungen ueber die diamagnetische Suszeptibilitaet einiger Organo(imino-oxy)silane; Monatshefte fuer Chemie, vol. 107, No. 2, 1976, pp. 531-535.

Singh, et al., Synthesis and Characterisation of Some Organo(imino-Oxy)Silanes; Journal of the Chemical Society, Dalton No. 17, 1972, pp. 1911-1913.

Singh, et al., Organometallic oximes and allied derivatives, Preparation and Characterization of some New Tris((iminoxy) Organosilanes, Chemical Abstracts; vol. 84, No, 7, No. 84:44260y Feb. 16, 1976.

Rupani, et al.; Synthesis and Characterization of Some New Organo(Iminoxy)silanes; Chemical Abstracts, vol. 92, No. 17 Apr. 28, 1980, abstract No. 92-146832u.

*Primary Examiner*—Melvyn I. Marquis
*Assistant Examiner*—Karen A. Dean
*Attorney, Agent, or Firm*—Jay P. Friedenson

[57] ABSTRACT

The invention relates to the following novel silanes: methyl vinyl bis(methyl isobutyl ketoximino) silane; methyl vinyl bis-(methyl amyl ketoximino) silane; methyl tris-(methyl isobutyl ketoximino) silane; vinyl tris-(methyl isobutyl ketoximino) silane; methyl tris-(methyl amyl ketoximino) silane; vinyl tris-(methyl amyl ketoximino) silane; tetrakis-(methyl isobutyl ketoximino) silane; tetrakis-(methyl amyl ketoximino) silane methoxy tris-(methyl isobutyl ketoximino) silane; ethyl tris-(methyl isobutyl ketoximino) silane; ethoxy tris-(methyl isobutyl ketoximino) silane; methoxy tris-(methyl amyl ketoximino) silane; ethyl tris-(methyl amyl ketoximino) silane; ethoxy tris-(methyl amyl ketoximino) silane; and mixtures thereof.

8 Claims, No Drawings

DI-, TRI- AND TETRAFUNCTIONAL METHYL ISOBUTYL AND METHYL AMYL KETOXIME-BASED SILANES

This application is a continuation-in-part of U.S. patent application Ser. No. 07/947,015, filed Sep. 17, 1992, which is incorporated herein by reference, now U.S. Pat. No. 5,359,108.

BACKGROUND OF THE INVENTION

A variety of useful silicone compositions cure at room temperature to elastomeric materials which possess a broad spectrum of physical and chemical properties. These compositions are particularly desirable because they surface cure in thirty minutes or less after exposure to the atmosphere but remain substantially soft for years. They also adhere tenaciously to a wide variety of materials such as glass, porcelain, wood, metal and organic plastics. Because of this, they are adaptable for practically any type of sealant application including building and automotive equipment applications. The following patents discuss some of these compounds in more detail.

U.S. Pat. No. 3,189,576 to Sweet describes oxime silanes useful in the manufacture of room temperature curing compositions. Specifically, Sweet teaches trifunctional and tetrafunctional ketoximino silanes as crosslinkers and their use in the manufacture of room temperature curing silicone elastomeric compositions by mixing them with hydroxyl endblocked polydiorganosiloxanes. These compositions can also contain fillers and curing catalysts.

U.S. Pat. No. 4,503,210 to Von Au discloses mixtures of tri- and tetrafunctional ketoximino silanes and focuses specifically on the usefulness of tetrafunctional ketoximino silanes in sealant formulations.

The problem with known tetrafunctional oximino silanes (i.e., e.g., those based on methyl ethyl ketoxime (MEKO) and acetone oxime) is that they are solids at room temperature. Since such compounds are very sensitive to moisture they decompose easily to semisolids which are difficult to handle. Thus, these materials have a poor shelf life and require special care in their packaging and transporting.

The known tetrafunctional and trifunctional oximino silanes (i.e., e.g., those based on MEKO and acetone oxime) have other drawbacks. Traditionally, when these materials have been combined with silicone polymers the resulting product has been opaque. This has substantially limited the applications in which these materials can be used.

As the applications in which room temperature curing compositions can be utilized continue to increase, the specific kinds of properties required of these compositions continue to change. The art is continually looking for room temperature curing compositions having new desirable properties without the old undesirable properties like opacity and physical state limitations (solids). We have surprisingly discovered that the silanes of the invention satisfy this need in the art.

DESCRIPTION OF THE INVENTION

The invention relates to silanes of the formula: $(R'R''C=NO)_a SiR1_{4-a}$ where R' is any saturated straight chain or branched alkyl radical of 3 to 7 carbon atoms such as propyl, isopropyl, butyl, isobutyl and amyl; R'' is methyl; and R1 is any saturated, straight chain alkyl or alkoxy radical of 1 to 8 carbon atoms such as methyl, ethyl and propyl or an alkenyl radical of 1 to 5 carbon atoms such as methyl, vinyl and allyl and a is a positive integer ranging in value from 2 to 4. More specifically, the invention relates to the following silanes: methyl vinyl bis(methyl isobutyl ketoximino) silane; methyl vinyl bis-(methyl amyl ketoximino) silane; methyl tris-(methyl isobutyl ketoximino) silane; vinyl tris-(methyl isobutyl ketoximino) silane; methyl tris-(methyl amyl ketoximino) silane; vinyl tris-(methyl amyl ketoximino) silane; tetrakis-(methyl isobutyl ketoximino) silane; tetrakis(methyl amyl ketoximino) silane; methoxy tris-(methyl isobutyl ketoximino) silane; ethyl tris-(methyl isobutyl ketoximino) silane; ethoxy tris-(methyl isobutyl ketoximino) silane; methoxy tris-(methyl amyl ketoximino) silane; ethyl tris(methyl amyl ketoximino) silane; ethoxy tris-(methyl amyl ketoximino) silane; and mixtures thereof.

In a preferred embodiment, the ketoxime silanes are selected from methoxy tris-(methyl isobutyl ketoximino) silane; ethoxy tris-(methyl isobutyl ketoximino) silane; methoxy tris-(methyl amyl ketoximo) silane; and ethoxy tris-(methyl amyl ketoximo) silane. In another preferred embodiment, the ketoxime silane is a mixture of tetrakis-(methyl isobutyl ketoximino) silane and at least one of methoxy tris-(methyl isobutyl ketoximino) silane; ethoxy tris-(methyl isobutyl ketoximino) silane; methoxy tris-(methyl amyl ketoximino) silane; ethoxy tris-(methyl amyl ketoximino) silane methyl tris-(methyl isobutyl ketoximino)silane and methyl tris-(methyl amyl ketoximino) silane. A one-component room-temperature-curing-system may be prepared by reacting a silane of the above formula with a hydroxy-endblocked siloxane polymer in the substantial absence of moisture. In another preferred embodiment of the invention, in the ketoxime silanes of the above formula, R1 has 1 to 5 carbon atoms.

As currently used in sealant compounding, commercial tetra-functional oximino silanes are either mixed (dissolved) in trifunctional oximino silanes as described in U.S. Pat. No. 4,503,210 or dissolved in organic solvents.

In the former case solubility limits the level of tetrafunctional oximino silane in the trifunctional oximino silane to 35–40% at room temperature. This is disadvantageous because higher levels of tetrafunctional oximino silane increase cure rate and minimize (if not eliminate) the need for a catalyst.

In the latter case, solid tetrafunctional oximino silanes are mixed with hydrocarbons like toluene, benzene and xylene, organic ethers like diethylether and dibutylether, ketones and halogenated solvents to facilitate ease of handling in applications which require precise amounts of tetrafunctional oximino silane. Because some of these solvents are flammable and carcinogenic, further precautions must be taken to ensure the satiety of personnel during processing. In addition, one must ensure that the vapor emissions from the finished sealant products generated during end use are safe :for people and the environment. These precautions are both costly and time consuming.

Solubility is also a concern. That is, for example, at room temperature, tetrafunctional MEKO-based silane is only 50% soluble in toluene and in methyl ethyl ketoxime, 40% soluble in diethyl ether and 10% soluble in dibutyl ether. As a result, significant amounts of solvent may be required in the formulation. In addition, crystallization can occur at lower temperatures (i.e., e.g., during shipping in winter months) and at higher concentrations of the tetrafunctional oximino silane.

Because of this, there has been a long felt need in the industry for tetrafunctional oximino silanes which do not require organic solvents or mixing with trifunctional oximino silanes. We have surprisingly discovered that the novel tetrakis oximino silanes of our invention, e.g. tetrakis-(methyl isobutyl ketoximino) silane and tetrakis-(methyl amyl ketoximino)silane are liquids and thus do not suffer with the same problems as their solid counterparts. These new silanes offer the ability to employ solvent-free formulations, if not significantly decrease solvent content in the composition. In addition, there is added flexiblity and simplification when formulating room temperature moisture-curable silicone compositions. Because the new silanes are liquid tetrafunctional oximino silanes, one can add more of these silanes to increase the cure rate of the composition. The amount of other tetrafunctional oximino silanes which can be used in this type of silicone composition is limited by their solubility in the solvent.

That the novel tetrafunctional oximino silanes are liquid is surprising since generally, physical states of organic compounds transform from gas to liquid to solid as molecular weight increases in a homologous series. See, R. T. Morrison and R. N. Boyd, *Organic Chemistry*, 91-4 (5th Ed. 1987). For example, in the aliphatic hydrocarbon series, lower molecular weight compounds like propane (MW 44) and butane (MW 58) are gases, higher molecular weight hydrocarbons like hexane (MW 86) and octane (MW 114) are liquids and the long chain hydrocarbon paraffins like eicosane (MW 282.6), docosane (MW 316.6) and tetracosane (MW 338.7) are solids.

In the instant case, since tetrafunctional oximino silanes of lower molecular weight alkyl ketoximes like acetone oxime (MW 73) and methyl ethyl ketoxime (MW 87) are solids, we also expected tetrafunctional oxime silanes of methyl isobutyl ketoxime and methyl amyl ketoxime which have higher molecular weights (115 and 129 respectively) to be solids. However, surprisingly, we discovered that both the tetrafunctional oximino silanes of the invention, are liquids at room temperature.

In addition to the novel liquid tetrafunctional oximino silanes, we have also discovered unexpectedly, that when oximino silanes (tetra-oximino, tris-oximino or bis-oximino) of the invention are formulated with hydroxyl terminated polydimethylsiloxane (HTPDMS), a well known silicone polymer, an optically clear silicone rubber results. This is surprising because generally when commercially available oxime silanes have been combined in typical and useful concentrations with silicone polymers, a very cloudy and opaque rubber results. (Compare Examples 1–9 with Comparative, Examples 1–4 below). This has limited the number of applications in which these materials can be utilized. In light of our discovery, the door is now open to a variety of applications in which aesthetics are important and from which oxime silanes have traditionally been excluded.

The novel ketoximino silanes of the invention may be prepared by following the syntheses outlined below. See, U.S. Pat. No. 4,400,527. Alternately, they may be prepared by any means known in the art. We note that the oximes used in the syntheses below may be prepared by any means known in the art. See, for example, the syntheses outlined in U.S. Pat. Nos. 4,163,756 and 3,991,115 both to Allied-Signal Inc.

The novel silanes of this invention can be used in combination with other crosslinking agents, which include other oximino silanes as well as alloxy silanes and alkoxy-oximino silanes. Examples of such silanes are dislosed in the following publications: U.S. Pat. Nos. 3,697,568; 3,896,079; 4,371,682 and 4,657,967.

Preparation of tetrakis-(methyl isobutyl ketoximino) silane.

A 1 liter 3-necked flask equipped with a condenser, thermometer and dropping funnel was charged with 350 ml of hexane and 96.7 g (0.84 mol) of distilled methyl isobutyl ketoxime. A drierite tube was attached to the condenser to ensure a dry reaction medium. The reaction flask was then placed in a cold water bath. While the hexane/ketoxime solution was stirred using a magnetic stirrer, 17 g (0.1 mol) tetrachloro silane was added dropwise into the reaction flask. The reaction temperature was maintained between 35° and 42° C. during the addition. After the addition of tetrachloro silane was complete, the reaction mixture was stirred for 5 minutes and then allowed to settle for 5 minutes. The colorless hexane solution top phase was separated from the viscous methyl isobutyl ketoxime hydrochloride bottom phase using a separatory funnel. The top phase was then treated with anhydrous ammonia gas from a cylinder for 10 minutes. The solid ammonium chloride that separated out was filtered off and the colorless filtrate was subjected to distillation under reduced pressure (50° C. at 5 mm Hg) on a rotovap to remove hexane. About 42 g (8.6%) yield) of a colorless liquid was obtained. The identity of this material as tetrakis-(methyl isobutyl ketoximino) silane was confirmed by proton and carbon-13 NMR and GC/Mass spectral data.

Preparation of tetrakis-(methyl amyl ketoximino) silane.

A 2 liter three-necked round bottom flask, fitted with an addition funnel, condenser and thermometer, was charged with 1300 ml of hexane and 418.6 g (3.24 mol) of methyl amyl ketoxime. While the solution was being stirred by means of an overhead stirrer, 67.96 g (0.4 mol) of tetrachloro silane was added dropwise over a period of 30 minutes during which time the reaction temperature was kept between 37°–42° C. After the tetrachloro silane had been added, the reaction mixture was allowed to stand for five minutes. The cloudy top phase was separated from the methyl amyl ketoxime hydrochloride bottom phase using a separatory funnel. Then, the top phase was neutralized with anhydrous ammonia over a period of 15 minutes and the solid ammonium chloride produced was filtered off. The hexane was removed from the filtrate under vacuum to give 178.5 g (82.6%) of a liquid. The identity of this liquid was confirmed as tetrakis-(methyl amyl ketoximino) silane by IR and proton and carbon-13 NMR spectral data.

PREPARATION OF ALKOXY-OXIMINO SILANES MIXTURE

Reaction of tetrachlorosilane:ethanol:methyl amyl ketoxime at 1:1:7 mole ratio:

A 1 liter 3-necked flask equipped with a condenser, dropping funnel and reflux condenser fitted with a drying tube was charged with 348 gms of hexane, 11.5 g (0.25 mol) of ethanol and 232.2 g (1.80 molt) of distilled methyl amyl ketoxime. While the alcohol, oxime and hexane solution was stirred using a overhead mechanical stirrer, 42.5 g (0.25 mol) of tetrachlorosilane was added dropwise into the reaction flask. During the addition, the reaction temperature was maintained between 35° and 42° C. After the addition of tetrachlorosilane was completed, the reaction mixture was stirred for 5 minutes and then allowed to settle for 5 minutes. The top phase was separated from the viscous methyl amyl ketoxime hydrochloride bottom phase using a separatory funnel. The top phase was neutralized with ammonia gas from a cylinder for 10 minutes. The precipitated ammonium chloride solid was separated by filteration. The clear colorless filterate was stripped of hexane to give 94.0 g of a colorless liquid. Gas chromatographic analysis of the liquid showed that it contained triethoxy(methyl amyl ketoximino) silane (5.6%), diethoxybis(-methyl amyl ketoximino) silane (12.5%), ethoxytris(-methyl amyl ketoximino) silane (43.2%), tetrakis (methyl amyl ketoximino) silane (33.9%) and methyl amyl ketoxime (4.5%). The identify of these silanes were confirmed by GC-mass spec analysis.

Preparation of methyl tris-(methyl isobutyl ketoximino) silane.

A 5 liter, three-necked and water jacketed flask, fitted with thermometer, overhead stirrer and addition funnel, was charged with 714.3 g (6.20 mol) of methyl isobutyl ketoxime and 3000 ml of hexane. One mole or 149.48 g of methyltrichlorosilane was added dropwise over a period of 1 hour during which the reaction temperature was maintained between 37°–42° C. After the addition of methyltrichlorosilane was complete, the reaction mixture was stirred for 5 minutes and allowed to stand for 10 minutes. The told phase was separated from the methyl isobutyl ketoxime hydrochloride bottom phase using a separatory funnel and neutralized with ammonia gas by bubbling the ammonia through the liquid for 10 minutes. Solid ammonium chloride was filtered off and hexane was removed from the filtrate by vacuum distillation to give 380 g (98.7%) of a colorless liquid. The identity of the product as methyl tris-(methyl isobutyl ketoximino) silane was confirmed by IR and proton and carbon-13 NMR spectral data.

Preparation of vinyl tris-(methyl isobutyl ketoximino) silane.

A 3 liter, three-necked, round bottomed flask equipped with an overhead stirrer, thermometer and addition funnel was charged with 714.0 g (6.20 mol) of methyl isobutyl ketoxime and 1200 ml of hexane. While stirring, 161.5 g (1.0 mol) of vinyltrichlorosilane was added dropwise over a period of 1 hour and the reaction temperature was maintained between 37°–41° C. After the addition was complete, the reaction mixture was allowed to stand for 10 minutes. The top phase containing product and hexane was separated from the bottom phase (methyl isobutyl ketoxime hydrochloride) using a separatory funnel and neutralized with ammonia gas for 10–15 minutes. Solid ammonium chloride was filtered off and hexane was removed from the filtrate by distilling under reduced pressure to give 374 g (94%) of a colorless liquid. The identity of this liquid as vinyl tris-(methyl isobutyl ketoximino) silane was confirmed by IR and proton and carbon-13 NMR spectral data.

Preparation of methyl tris-(methyl amyl ketoximino) silane.

A 2 liter, three-necked, round bottomed flask, fitted with a thermometer, overhead stirrer and addition funnel was charged with 394.1 g (3.05 mol) of methyl amyl ketoxime and 1000 ml of hexane. While stirring the contents in the flask, 74.5 g (0.5 mol) of methyltrichlorosilane was added dropwise from the addition funnel over a period of 30 minutes. During the addition, the reaction temperature was maintained at 35°–41° C. After the addition was complete, the reaction mixture was allowed to stand for 10 minutes. The top phase containing hexane and the product was separated from the heavy methyl isobutyl ketoxime hydrochloride bottom phase using a separatory funnel. The top phase was neutralized with ammonia gas by bubbling the ammonia through the liquid for 10 minutes. Solid ammonium chloride was filtered off and hexane was removed from the filtrate by distillation under reduced pressure to give 201.8 g (94.5%) of a colorless liquid. This liquid was identified by IR and proton and carbon 13 NMR spectral data as methyl tris-(methyl amyl ketoximino) silane.

Preparation of vinyl tris-(methyl amyl ketoximino) silane.

A 2 liter, three-necked flask fitted with overhead stirrer, addition funnel and thermometer was charged with 236.4 g (1.83 mol) of methyl amyl ketoxime and 800 ml of hexane. While the contents of the flask were stirred, 48.45 g (0.3 mol) of vinyl-trichlorosilane was added dropwise, from the addition funnel over a period of 30 minutes during which the reaction temperature was maintained between 32°–41° C. After the addition of vinylchlorosilane was complete, the reaction mixture was allowed to stand for 10 minutes. The top phase containing product and hexane was separated from the heavy bottom phase (methyl amyl ketoxime hydrochloride) using a separatory funnel and neutralized with ammonia gas by bubbling the ammonia through the liquid for 10 minutes. Ammonium chloride was filtered to give a clear filtrate. Hexane was removed from the filtrate by distilling under reduced pressure to give 115 g (87%) of a colorless liquid which was identified as vinyl tris-(methyl amyl ketoximino) silane by IR and proton and carbon-13 NMR spectral data.

Preparation of methyl vinyl bis-(methyl isobutyl ketoximino) silane

Into a 500 ml, three-necked flask, fitted with thermometer, condenser and dropping funnel, was charged a solution of 47.17 g (0.41 mol) of methyl isobutyl ketoxime and 250 ml of hexane. While stirring this mixture by means of a magnetic stirrer, 14.11 g (0.1 mol) of methyl vinyl dichlorosilane was added dropwise from the addition funnel over a period of 15 minutes. The reaction temperature was maintained between 33°–38° C. After the addition of chlorosilane was complete, the reaction mixture was allowed to stand for 5 minutes during which the phases separated. The top phase was separated from the oxime hydrochloride bottom phase by means of a separatory funnel. The top phase was neutralized with ammonia gas by bubbling the ammonia through the liquid for 10 minutes and the precipitated ammonium chloride was filtered off. Hexane from the filtrate was removed by distillation under reduced pressure to give 27.5 g (89%) of a colorless liquid which was identified as methyl vinyl bis-(methyl isobutyl ketoximino) silane by IR and proton and carbon-13 NMR spectral data.

Preparation of methyl vinyl bis-(methyl amyl ketoximino) silane

A 3 liter, three-necked flask fitted with an overhead stirrer, addition funnel and thermometer was charged with 529 g (4.1 mol) of methyl amyl ketoxime and 1200 ml of hexane. While stirring the contents of the flask, 141 g (1.0 mol) of methyl vinyl dichlorosilane was added dropwise from the addition funnel over a period of 40 minutes during which the reaction temperature was maintained between 28°–32° C. After the addition was complete, the reaction mixture was allowed to stand for 10 minutes to form two phases. The top phase containing product and hexane was removed from the oxime hydrochloride heavy phase using a separatory funnel and neutralized with ammonia gas by bubbling the ammonia through the liquid for 10 minutes. Ammonium chloride solid was filtered and hexane was removed from the filtrate by distillation under reduced pressure to give 286 g (87.7%) of a colorless liquid. This liquid was identified as methyl vinyl bis(methyl amyl ketoximino) silane by IR and proton and carbon-13 NMR spectral data.

EXAMPLE 1

To a 100 ml beaker was added 50 parts by weight of hydroxyl terminated polydimethylsiloxane (HTPDMS) having a viscosity of 50,000 cst. Then, 1–4 parts by weight of methyl tris-(methyl isobutyl ketoximino) silane (prepared in accordance with the synthesis disclosed herein) was added. The compounds were mixed at 25° C. at 200 rpm using a standard laboratory stirrer for 5 minutes. The resulting product cured to a clear silicone robber.

EXAMPLE 2–9

The experiment outlined in Example 1 above, was repeated using the following silanes:

1.) 1–4 parts by weight methyl tris-(methyl amyl ketoximino) silane;
2.) 2–3 parts by weight vinyl tris-(methyl amyl ketoximino) silane;
3.) 2–3 parts by weight vinyl tris-(methyl isobutyl ketoximino silane);
4.) 1–3 parts by weight tetrakis-(methyl amyl ketoximino) silane;
5.) 1–3 parts by weight tetrakis-(methyl isobutyl ketoximino) silane;
6.) 3:1 parts by weight of a mixture of methyl tris-(methyl isobutyl ketoximino) silane and tetrakis-(methyl isobutyl ketoximino) silane;
7.) 3:1 parts by weight of a mixture of methyl tris-(methyl amyl ketoximino) silane and tetrakis-(methyl amyl ketoximino) silane;
8.) 3:1 parts by weight of a mixture of methyl tris-(methyl amyl ketoximino) silane and tetrakis-(methyl isobutyl ketoximino) silane; The results were the same as those reported in Example 1. That is, the resulting cured silicone rubber was clear.

Comparative Example 1

To a 100 ml beaker was added 50 parts by weight of HTPDMS, having a viscosity of 50,000 cst. Then, 3–4 parts by weight of methyl tris-(methyl ethyl ketoximino) silane was added. The compounds were mixed at 25° C. and 200 rpm using a standard laboratory stirrer for 5 minutes. The resulting product cured to an opaque, cloudy silicone rubber.

Comparative Examples 2–4

The procedure outlined in Comparative Example 1 was repeated using the following silanes:

1.) 2–10 parts by weight vinyl tris-(methyl ethyl ketoximino) silane;
2.) 3–10 parts by weight tetrakis-(methyl ethyl ketoximino) silane in toluene;
3.) 3:1 parts by weight of a mixture of methyl tris-(methyl ethyl ketoximino) silane and tetrakis-(methyl ethyl ketoximino) silane. The results are the same as those reported for Comparative Example 1. That is, the resulting product cured to an opaque, cloudy silicone rubber.

The silanes of the invention have utility as intermediates in the preparation of various one-component room-temperature-curing compositions for sealant, adhesive, coating and other silicone polymer applications. These one-component systems may be prepared in accordance with the teachings of U.S. Pat. No. 3,189,576 to Sweet (Example 17 at col. 12, lines 6–26) and U.S. Pat. No. 4,720,530 to Wurminghause et al. at col. 1, lines 60–67 and col. 2, lines 1–43 which disclosure is hereby incorporated herein by reference. Generally, the method for preparing one-component room-temperature-curing compositions comprises reacting in the substantial absence of moisture a hydroxy-endblocked siloxane polymer with a silane. Optionally, fillers such as silica, chalk and glass beads, adhesion promotors such as organofunctional silanes and catalysts such as tin carboxylates, dibutyl tin diacetate, and dibutyl tin dilaurate, lead carboxylates, zinc carboxylates and organo titanates may be included in these formulations.

What is claimed:

1. Ketoxime silanes of the formula:
   $(R'R''C=NO)_a SiR1_{4-a}$ where $R'$ is any saturated straight chain or branched alkyl radical of 3 to 7 carbon atoms; $R''$ is methyl; and R1 is any alkoxy radical of 1 to 8 carbon atoms and a is a positive integer ranging in value from 2 to 4.

2. Ketoxime silanes of claim 1 wherein $R'$ is selected from propyl, isopropyl, butyl, isobutyl and amyl.

3. Ketoxime silanes of claim 1 wherein the silanes are selected from:
   methoxy tris-(methyl isobutyl ketoximino) silane; ethoxy tris(methyl isobutyl ketoximino) silane; methoxy tris-(methyl amyl ketoximino) silane; ethoxy tris-(methyl amyl ketoximino) silane; and mixtures thereof.

4. The ketoxime silanes of claim 1 wherein said silane is selected from methoxy tris-(methyl isobutyl ketoximino) silane and ethoxy tris-(methyl isobutyl ketoximino) silane.

5. The ketoxime silanes of claim 1 wherein said silane is selected from methoxy tris-(methyl amyl ketoximo) silane and ethoxy tris-(methyl amyl ketoximo) silane.

6. The ketoxime silanes of claim 1 wherein said silane is a mixture of tetrakis-(methyl isobutyl ketoximino) silane and at least one of methoxy tris-(methyl isobutyl ketoximino) silane and ethoxy tris-(methyl isobutyl ketoximino) silane.

7. The ketoxime silanes of claim 1 wherein said silane is a mixture of tetrakis-(methyl isobutyl ketoximino) silane and at least one of methoxy tris-(methyl amyl ketoximino) silane and ethoxy tris-(methyl amyl ketoximino) silane.

8. The ketoxime silanes of claim 1 wherein R1 has 1 to 5 carbon atoms.

* * * * *